United States Patent
Bruun

(10) Patent No.: US 11,963,944 B2
(45) Date of Patent: *Apr. 23, 2024

(54) CANNABINOID POUCH

(71) Applicant: NordicCan, Vejle (DK)

(72) Inventor: Heidi Ziegler Bruun, Vejle Ost (DK)

(73) Assignee: NordicCan A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/988,412

(22) Filed: Nov. 16, 2022

(65) Prior Publication Data

US 2023/0078188 A1 Mar. 16, 2023

Related U.S. Application Data

(63) Continuation of application No. 16/625,505, filed as application No. PCT/DK2017/050209 on Jun. 23, 2017, now Pat. No. 11,534,421.

(51) Int. Cl.

| | |
|---|---|
| *A61K 31/353* | (2006.01) |
| *A61K 9/00* | (2006.01) |
| *A61K 31/05* | (2006.01) |
| *A61K 47/02* | (2006.01) |
| *A61K 47/12* | (2006.01) |
| *A61K 47/26* | (2006.01) |

(52) U.S. Cl.
CPC ............ *A61K 31/353* (2013.01); *A61K 9/009* (2013.01); *A61K 31/05* (2013.01); *A61K 47/02* (2013.01); *A61K 47/12* (2013.01); *A61K 47/26* (2013.01)

(58) Field of Classification Search
CPC ...... A61K 47/02; A61K 9/009; A61K 31/353; A61K 9/0056; A61K 47/26; A61K 31/352; A61K 31/05; A61K 47/12; A61K 9/0053

See application file for complete search history.

(56) References Cited

U.S. PATENT DOCUMENTS

| | | | | |
|---|---|---|---|---|
| 11,007,170 B2* | 5/2021 | Segal | .................... | A61K 36/185 |
| 2004/0009232 A1* | 1/2004 | Reiner | ................. | A61K 9/1623 |
| | | | | 424/499 |
| 2009/0293895 A1* | 12/2009 | Axelsson | ............. | A61K 31/465 |
| | | | | 131/352 |
| 2013/0098377 A1* | 4/2013 | Borschke | ................ | A61K 25/26 |
| | | | | 514/343 |
| 2013/0251779 A1* | 9/2013 | Svandal | .................. | A61P 25/34 |
| | | | | 424/440 |
| 2015/0057342 A1 | 2/2015 | Koren et al. | | |
| 2015/0094322 A1* | 4/2015 | Riel | ....................... | A61P 43/00 |
| | | | | 514/460 |
| 2016/0015683 A1 | 1/2016 | McCarty | | |
| 2016/0165953 A1 | 6/2016 | Goode, Jr. | | |
| 2016/0220593 A1 | 8/2016 | Anastassov et al. | | |
| 2017/0172927 A1 | 6/2017 | Fusco et al. | | |

FOREIGN PATENT DOCUMENTS

| | | | | |
|---|---|---|---|---|
| WO | 2015117011 | A1 | 8/2015 | |
| WO | WO-2015117011 | A1 * | 8/2015 | ............... A23F 3/14 |
| WO | 2017059859 | A1 | 4/2017 | |
| WO | 2018233782 | A1 | 12/2018 | |

OTHER PUBLICATIONS

Vehovec et al., "Influence of different types of commercially available microcrystalline cellulose on degradation of perindopril bumine and enalapril maleate in binary mixtures", Acta Pharm. 62 (2012) 515-528. (Year: 2012).*

Remington's Pharmaceutical Sciences 17, 1985, Mack Publishing Company, Excerpt from p. 655, first column.

* cited by examiner

*Primary Examiner* — Jianfeng Song

(74) *Attorney, Agent, or Firm* — Murtha Cullina LLP

(57) ABSTRACT

A pouch designed for administration of an active ingredient in the oral cavity is disclosed, the pouch containing a powder composition having an amount of one or more cannabinoids and a water-insoluble composition including cellulose and/or fibers in the form of particles in an amount of 30 to 80% by weight of the powder composition. The powder composition further includes a water-soluble composition comprising one or more sugar alcohols and the pouch includes a water-permeable membrane. A pouch designed for administration of an active ingredient in the oral cavity is also disclosed.

19 Claims, No Drawings

CANNABINOID POUCH

FIELD OF INVENTION

The invention relates to pouches comprising cannabinoids.

BACKGROUND OF THE INVENTION

Cannabinoids or derivatives thereof have been used for medical purposes.

Cannabis is often administering by smoking. A problem related to such administration is that the rapid absorption into the blood via the lung may be undesirable. Not only may the smoking as such have side effects, but the administration may be difficult to manage.

SUMMARY OF THE INVENTION

The invention relates to a pouch designed for administration of an active ingredient in the oral cavity,
the pouch containing a matrix composition comprising a combination of an amount of one or more cannabinoids and a water-insoluble composition.

According to the invention, the matrix composition in the pouch comprises one or more cannabinoids as the active ingredient. The pouch also comprises a membrane or barrier defining an inner space sealed by the membrane. This membrane or barrier is water-permeable, so that, when in use, the saliva enters the inner space through the membrane or barrier, where the one or more cannabinoids are dissolved or otherwise mobilized by the saliva. Then, the saliva and the mobilized or dissolved cannabinoid(s) may cross the membrane again thereby releasing the one or more cannabinoids and the optional other substances to the oral cavity.

On the other hand, the water-insoluble composition may be retained inside the pouch even during use due to a combination of its water-insoluble characteristics and e.g. a larger dimension of the water-insoluble composition, for examples as a powder composition, compared to the openings of the membrane. In other words, a pouch with a matrix composition may be provided that, during use, release said one or more cannabinoids while retaining the water-insoluble composition. In this way, according to an embodiment, the water-insoluble composition may be affect the release of said one or more cannabinoids in a manner so as to achieve a prolonged release, allowing the user to feel the effect of the released cannabinoids and thus control the release total dose of cannabinoids by removing and optionally re-inserting the pouch in order to achieve the desired effect.

One challenge with respect to dosing of cannabinoids is that the desired effect on a particular individual depends on several factors apart of the dose itself, for example the body weight of the individual and other factors affecting the how a certain dose translates into a specific plasma concentration, but also the efficiency of the cannabinoids which may be lowered after prolonged use and differ from person to person. Finally, the symptoms experienced by a specific user may also differ from time to time and thus a suitable dose one day may be too high or too low the next day. Consequently, it is desirable that a person can self-adjust the dose according to the individual circumstances of the specific situation. However, one challenge here may be that premetered standard doses may not necessarily fit the needs of the individual user, whereas more customized doses are expensive in distribution and inconvenient in handling.

Finally, due to the delay of the effect experienced by the user after administration of one pouch to the oral cavity may cause the user to insert a second pouch in the oral cavity, after which the experienced effect becomes higher than intended.

The present invention provides a pouch system for efficient and fast release of cannabinoids circumventing the metabolic system and allowing the user to adjust the dose to the specific need, by allowing the dose of cannabinoids released to be adjusted by the usage time. Other systems may rely on single dose administrations, such as ingestible pills, fast dissolving delivery platforms etc. The present invention, however, provides a much more flexible delivery vehicle while avoiding the disadvantages associated with e.g. smoking marijuana, as e.g. inhalation of carcinogenic substances.

Critical for the invention is the combined presence in the matrix composition of both the one or more cannabinoids and also the water-insoluble composition. The insoluble composition may preferably work to delay the release of said one or more cannabinoids for example in the sense that the one or more cannabinoids are bound to the water-insoluble composition so as to act as a carrier, or by controlling the release of the one or more cannabinoids by, during use, controlling the access of water or saliva to the one or more cannabinoids.

One important aspect of the invention is that both the one or more cannabinoids and the water-insoluble composition must be present in the pouch. The combination of the cannabinoids and the water-insoluble composition allows the cannabinoids to be released, advantageously under influence of the water-insoluble composition. The water-insoluble composition may therefore act as a carrier or be part of a carrier, e.g. by the cannabinoids being bound or adhered to the carrier. Alternatively, the cannabinoids may be distributed between the water-insoluble composition, i.e. interspersed between the water-insoluble composition, such that the water-insoluble composition forms a matrix or forms part of a matrix for the one or more cannabinoids. Thus, the carrier may function by influencing the release of the cannabinoids and/or by stabilizing the cannabinoids before release.

According to an embodiment of the invention, the pouch comprise a further active ingredient other than said one or more cannabinoids.

According to an embodiment of the invention, the pouch consists of said matrix composition and a sealed barrier enclosing said matrix composition.

According to an advantageous embodiment of the invention the matrix composition comprises said water-insoluble composition in an amount of between 1 and 80 percent weight of said matrix composition.

According to an embodiment of the invention, the matrix composition comprises said water-insoluble composition in an amount of between 2 and 70 percent weight of said matrix composition.

According to an embodiment of the invention, the matrix composition comprises said water-insoluble composition in an amount of between 3 and 60 percent weight of said matrix composition.

According to an embodiment of the invention, the matrix composition comprises said water-insoluble composition in an amount of between 5 and 50 percent weight of said matrix composition.

According to an advantageous embodiment of the invention the water-insoluble composition comprises a water-insoluble carrier.

One advantage of the above embodiment may be that a user controlled release of said one or more cannabinoids may be provided by means of said pouched product. This may facilitate a more individualized dosage of cannabinoids, by allowing each user to individually adjust the release dosage e.g. in view of the instantaneously experienced effect and/or previous experience. Also, by providing a relatively slow release of said cannabinoids, e.g. in combination with a relatively high total content of cannabinoids, an advantageous and individualized user controlled release of cannabinoids may be obtained.

A further advantage may be that a relatively effective and/or fast uptake of cannabinoids may be provided, due to a local high concentration around the pouch, thereby giving a relatively steep concentration gradient across the mucous membrane.

According to an embodiment of the invention, the water-insoluble composition is a water-insoluble carrier.

One advantage of the above embodiment may be that a relatively long-lasting release of said one or more cannabinoids may be obtained. By utilizing the water-insoluble carrier as a release prolonging measure, a slow release may be obtained, which for example allows the user to gradually feel the effect of the released cannabinoids and remove the pouch from the oral cavity when the desired effect has been obtained. Also, a slow release may allow the total amount of said one or more cannabinoids to be relatively high, without giving a too high release per time even at initiation of the use. For example, the total amount of said one or more cannabinoids may be adapted to cover more than one usage events, thereby allowing the user to remove and reinsert the pouch into the oral cavity as preferred.

According to an advantageous embodiment of the invention the water-insoluble composition comprises cellulose.

One advantage of the above embodiment may be that the water-insoluble composition comprises cellulose being both suitable as a carrier for the one or more cannabinoids and as a humectant.

According to an advantageous embodiment of the invention the cellulose is present in an amount of 5 to 60 percent of said matrix composition.

According to an embodiment of the invention the cellulose is present in an amount of 10 to 60 percent of said matrix composition.

According to an advantageous embodiment of the invention the water-insoluble composition comprises microcrystalline cellulose (MCC).

One advantage of the above embodiment may be that the water-insoluble composition comprises MCC being both suitable as a carrier for the one or more cannabinoids and as a humectant.

According to an advantageous embodiment of the invention the MCC is present in an amount of 5 to 60 percent of said matrix composition.

In an embodiment of the invention said cellulose is selected from the list consisting of microcrystalline cellulose (MCC); carboxymethylcellulose (CMC), such as sodium carboxymethylcellulose; hydroxypropyl methylcellulose (HPMC), methylcellulose; ethylcellulose (EC); methylethylcellulose (MEC); hydroxyethyl cellulose (HEC); hydroxyethyl methylcellulose (HEMC); and any combination thereof.

According to an embodiment of the invention the cellulose, such as microcrystalline cellulose forms a carrier, or part of.

According to an advantageous embodiment of the invention the water-insoluble composition comprises an ion-exchange resin.

One advantage of the above embodiment may be that a relatively high stability of said one or more cannabinoids may be obtained, e.g. comparing with not having any carrier.

According to an advantageous embodiment of the invention the ion-exchange resin is present in an amount of 5 to 60 percent of said matrix composition.

According to an embodiment of the invention the ion-exchange resin is present in an amount of 10 to 60 percent of said matrix composition.

According to an embodiment of the invention the ion-exchange resin is a carrier, or part thereof.

According to an advantageous embodiment of the invention the ion-exchange resin is a basic ion-exchange resin.

According to an embodiment of the invention the basic ion-exchange resin is a carrier, or part thereof.

According to an embodiment of the invention the basic ion-exchange resin is a strongly basic ion-exchange resin.

According to an embodiment of the invention the strongly basic ion-exchange resin is a carrier, or part thereof.

According to an embodiment of the invention, when using the basic ion-exchange resin, particularly when using a strongly basic ion-exchange resin, a pH-controlling agent, preferably an acidic pH-controlling agent or buffering agent, is added to the matrix composition. Thereby, an advantageous release of said one or more cannabinoids from the ion-exchange resin may be obtained by facilitating release from the basin ion-exchange resin.

According to an advantageous embodiment of the invention the matrix composition further comprises a water-soluble composition.

According to an advantageous embodiment of the invention the water-soluble composition comprises sugar alcohol.

According to an embodiment of the invention, said sugar alcohol may be a single type of sugar alcohol, or a mixture of two or more sugar alcohols.

According to an embodiment of the invention the water-soluble composition is sugar alcohol.

According to an advantageous embodiment of the invention said matrix composition comprises said sugar alcohol in an amount of 1 to 90 percent by weight of said matrix composition.

According to an embodiment of the invention said sugar alcohol in an amount of 5 to 80 percent by weight of said matrix composition.

Thus, according to one or more of the above embodiments, the matrix composition comprises the water-insoluble composition in combination with one or more further substances, such as a water-soluble composition, such as sugar alcohol.

According to an embodiment of the invention the water-soluble composition comprises sugar.

According to an embodiment of the invention said matrix composition comprises said sugar in an amount of 1 to 90 percent by weight of said matrix composition According to an embodiment of the invention, the water-soluble composition comprises a combination of sugar and sugar alcohol.

In some embodiments, the water-insoluble composition comprises a carrier, or forms a carrier.

According to an advantageous embodiment of the invention the matrix composition comprises a pH controlling agent.

An advantage of the above embodiment may be that the cannabinoids are released more effectively from the pouch.

This may be especially when the matrix composition comprises an ion exchange resin as a carrier for the one or more cannabinoids.

For example, the pH controlling agent may comprise or be a buffering agent, which is acidic, i.e. adapted to ensure a relatively low pH value in the oral cavity below 7 so as to ensure release of said one or more cannabinoids from an ion exchange resin. In the matrix composition, such pH controlling agents may be kept inactive by separating it from the complex between the one or more cannabinoids and the ion-exchange resin until activated by water from the saliva during use.

According to an advantageous embodiment of the invention the pH controlling agent is an acidic pH controlling agent and/or a basic pH controlling agent.

According to an advantageous embodiment of the invention the matrix composition further comprises a release controlling composition.

In an embodiment of the invention, the release controlling composition is provided as a powder composition having an average particle below the average particle size of the remaining matrix composition. E.g. the average particle size of the release controlling composition may be less than half of the average particle size of the remaining matrix composition. Especially in embodiments, where the matrix composition comprises a water-soluble composition, such as sugar alcohols, the average particle size of the release controlling composition may advantageously be smaller than the average particle size of the water-soluble composition, such as the sugar alcohols. Thereby, the release controlling composition may advantageously control the release of the water-soluble composition, if any, and/or the cannabinoids, e.g. by controlling the moistening of the pouch, i.e. the supply of saliva to the matrix composition.

According to an advantageous embodiment of the invention the release controlling composition is hydrophobic.

One advantage of the above embodiment may be that an effective control of the supply of water in the form of saliva may be obtained, thus giving control of the release.

According to an advantageous embodiment of the invention said release controlling composition comprises one or more metallic stearates.

According to an advantageous embodiment of the invention said release controlling composition comprises magnesium stearate.

According to an embodiment of the invention said release controlling composition comprises magnesium stearate.

According to an advantageous embodiment of the invention said release controlling composition comprises calcium stearate.

According to an advantageous embodiment of the invention the matrix composition comprises said release controlling composition in an amount of between 1 and 20 percent by weight of said matrix composition.

According to an embodiment of the invention the matrix composition comprises said release controlling composition in an amount of between 3 and 15 percent by weight of said matrix composition.

According to an embodiment of the invention the matrix composition comprises magnesium stearate as said release controlling composition in an amount of between 3 and 15 percent by weight of said matrix composition.

According to an advantageous embodiment of the invention the matrix composition is a powdered matrix composition.

According to an embodiment of the invention the water-insoluble composition is a powder composition.

For example, when the water-insoluble composition is a water-insoluble carrier, it may be provided as a powder composition.

According to an advantageous embodiment of the invention powdered matrix composition has an average particle size of below 1200 micrometer.

According to an advantageous embodiment of the invention powdered matrix composition has an average particle size of above 1 micrometer.

According to an embodiment of the invention, the powdered matrix composition as an average particle size is between 1 and 1200 micrometer.

In an embodiment of the invention the powdered matrix composition has an average particle size of said powdered composition is between 1 and 400 micrometer.

According to an embodiment of the invention, the average powder size is larger than the average opening dimension of the pouch.

According to an embodiment of the invention the characteristic opening dimension is adapted to the characteristic dimension of the matrix composition so as to retain the matrix composition inside the pouch before use and/or to retain the insoluble composition inside the pouch during use.

According to an advantageous embodiment of the invention the pouch comprises a water-permeable membrane, comprising e.g. wowen or non-wowen fabric.

According to an advantageous embodiment of the invention the one or more cannabinoids are on crystalline form.

According to an embodiment of the invention, the one or more cannabinoids comprises cannabidiol or consists of cannabidiol on crystalline form.

According to an advantageous embodiment of the invention the one or more cannabinoids are physically or chemically bound to at least a part of the matrix composition acting as a carrier.

According to an advantageous embodiment of the invention the one or more cannabinoids have been granulated with the carrier.

According to an advantageous embodiment of the invention the matrix composition comprises said one or more cannabinoids in an amount of between 0.1 and 50 percent weight of said matrix composition.

In embodiments, where a cannabinoid extract is used as a source of said one or more cannabinoids, the matrix composition may in some cases comprise a lower amount of cannabinoids, such as e.g. 0.1 to 30 percent by weight of the matrix composition, especially when a relatively diluted extract is used, i.e. where the content of cannabinoids is relatively low.

According to an advantageous embodiment of the invention the matrix composition comprises said one or more cannabinoids in an amount of 0.25 to 500 milligrams.

According to an advantageous embodiment of the invention said one or more cannabinoids are derived from cannabis.

In an alternative embodiment, the composition may comprise one or more cannabinoids, where one or all of the cannabinoids are not derived from cannabis and e.g. comprise synthetic cannabinoids.

According to an advantageous embodiment of the invention said one or more cannabinoids comprises at least two cannabinoids.

According to an advantageous embodiment of the invention said one or more cannabinoids consists of two cannabinoids.

Thus, according to the above embodiment, the matrix composition and the pouch is substantially free of further cannabinoids other than said two cannabinoids. Moreover, it should be understood according to the above embodiment that the pouch comprises a combination of two cannabinoids, i.e. a combination of two different types of cannabinoids. Further, the pouch according to the above embodiment comprises only two cannabinoids. In practical scenarios, it may not be easy to achieve complete elimination of certain substances, thus, there may in some embodiments be small or trace amounts of further cannabinoids, e.g. due to a small degree of degradation of the intended cannabinoid(s).

According to an advantageous embodiment of the invention said one or more cannabinoids consists of one cannabinoid, such as tetrahydrocannabinol or cannabidiol.

According to an advantageous embodiment of the invention the one or more cannabinoids comprise cannabidiol.

According to an advantageous embodiment of the invention said one or more cannabinoids comprises cannabidiol in an amount of between 10 and 100 percent by weight of the one or more cannabinoids.

In an embodiment of the invention the one or more cannabinoids comprises cannabidiol in an amount of between 20 and 100 percent by weight of the one or more cannabinoids.

In an embodiment of the invention the one or more cannabinoids comprises cannabidiol in an amount of between 30 and 90 percent by weight of the one or more cannabinoids.

In an embodiment of the invention the one or more cannabinoids comprises cannabidiol in an amount of between 50 and 90 percent by weight of the one or more cannabinoids.

In an embodiment of the invention the one or more cannabinoids comprises cannabidiol in an amount of between 70 and 99 percent by weight of the one or more cannabinoids.

In one embodiment, the one or more cannabinoids consists essentially of cannabidiol.

According to an advantageous embodiment of the invention the one or more cannabinoids comprise tetrahydrocannabinol.

According to an advantageous embodiment of the invention the one or more cannabinoids comprises tetrahydrocannabinol in an amount of between 10 and 100 percent by weight of the one or more.

In an embodiment of the invention the one or more cannabinoids comprises tetrahydrocannabinol in an amount of between 20 and 100 percent by weight of the one or more cannabinoids.

In an embodiment of the invention the one or more cannabinoids comprises tetrahydrocannabinol in an amount of between 30 and 90 percent by weight of the one or more cannabinoids.

In an embodiment of the invention the one or more cannabinoids comprises tetrahydrocannabinol in an amount of between 50 and 90 percent by weight of the one or more cannabinoids.

In an embodiment of the invention the one or more cannabinoids comprises tetrahydrocannabinol in an amount of between 70 and 99 percent by weight of the one or more cannabinoids.

In one embodiment, the one or more cannabinoids consists essentially of tetrahydrocannabinol.

According to an advantageous embodiment of the invention the pouch comprises a humectant.

In one embodiment the humectant may be the water-insoluble composition or be part of the water-insoluble composition, whereas in other embodiments it may be provided as a separate composition in the pouch. When the water-insoluble composition comprises a carrier or is part of a carrier, the humectant may be provided as the water-insoluble carrier or as a separate composition in the pouch.

Suitable humectants may include one or more hygroscopic materials, such as cellulose, sugar alcohols, and other hygroscopic materials.

According to an advantageous embodiment of the invention the humectant comprises one or more from the list consisting of sugar alcohol, alginate, cellulose, such as microcrystalline cellulose, pectin, xanthan gum.

The humectant may in one embodiment be provided separately from the water-insoluble composition.

The humectant may in one embodiment be provided by the water-insoluble composition, i.e. the water-insoluble composition is a humectant or comprises a humectant. When the water-insoluble composition comprises a carrier, or is part of a carrier, the carrier may be a humectant.

The invention further relates to the pouch according to the invention or any of its embodiments for use as a medicament.

The invention further relates to the pouch according to the invention or any of its embodiments for use in alleviation of pain.

According to an advantageous embodiment of the invention said pain is neurotic pain.

According to an advantageous embodiment of the invention said pain is cancer-related pain.

The invention further relates to the pouch according to the invention or any of its embodiments for use in mitigation of appetite deficiency.

The invention further relates to a method of alleviation of pain, such as neurotic pain or cancer-related pain, by administering an effective amount of said one or more cannabinoids by means of the pouch according to the invention or any of its embodiments.

The invention further relates to a method of mitigation of appetite deficiency by administering an effective amount of said one or more cannabinoids by means of the pouch according to the invention or any of its embodiments.

DETAILED DESCRIPTION OF THE INVENTION

As used herein the term "pouch" is intended to mean a container typically formed by a web of a fibrous material enclosing a cavity. The pouch is pouch designed for administration of an active ingredient in the oral cavity, and thus it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the one or more cannabinoids and the water-insoluble composition. In order to release the one or more cannabinoids, the pouch is made water-permeable so as to allow saliva from the oral cavity to penetrate the pouch and enter the cavity, where the saliva can come into contact with the one or more cannabinoids, whereby the one or more cannabinoids are released from the oral pouch.

As used herein the term "carrier" is intended to mean a substance that binds, physically or chemically an active ingredient. Unless otherwise stated, the term "carrier" refers to a carrier for said one or more cannabinoids. Examples of carriers include ion exchange resins, and cellulose, e.g. microcrystalline cellulose. The one or more cannabinoids may for example be granulated with the cellulose, when using cellulose as the water-insoluble composition. When using ion-exchange resin as the water-insoluble composition, the one or more cannabinoids are bound to the ion-exchange resin.

As used herein the term "cannabinoids" refers to cannabinoids derived from cannabis plants and synthetic cannabinoids. Examples of cannabinoids include cannabidiol, tetrahydrocannabinol, cannabinol, etc.

As used herein the terms "cannabidiol" and "CBD" both refer to Cannabidiol (IUPAC: 2-[(1R,6R)-6-isopropenyl-3-methylcyclohex-2-en-1-yl]-5-pentylbenzene-1,3-diol).

As used herein the terms "tetrahydrocannabinol" and "THC" both refer to Tetrahydrocannabinol, (−)-trans-$\Delta^9$-tetrahydrocannabinol (IUPAC: (−)-(6aR,10aR)-6,6,9-Tri methyl-3-pentyl-6a, 7,8,10a-tetrahydro-6H-benzo[c]chromen-1-ol).

As used herein the term "powder composition" refers to composition in the form of powder, i.e. as a particulate material having a relatively small average particle size, for example between 1 and 1200 micrometer.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include cellulose, such as microcrystalline cellulose and other cellulose types disclosed herein, sugar alcohols, such as those disclosed herein, alginate, cellulose, such as microcrystalline cellulose, pectin, xanthan gum, etc.

As used herein the term "water-insoluble composition" refers to a composition having a relatively low water-solubility, for example consisting of water-soluble substances having a water-solubility of less than 1 gram of water-insoluble composition per 100 mL of water measured at 25 degrees Celsius and pH of 7.0. When referring to an "insoluble" composition or substance, water-insoluble is meant, unless otherwise stated. Likewise, when referring to "soluble", water-soluble is meant unless otherwise stated. The water-insoluble composition is part of the matrix composition. In some embodiments, water-soluble composition is part of a carrier or forms such carrier.

As used herein the term "matrix composition" is used as reference to the total content of the pouch, i.e. the entire composition enclosed by the pouch. Typically, it therefore corresponds to the pouch excluding the outer membrane of the pouch.

Typically, the pouches comprise openings, where the characteristic opening dimension is adapted to a characteristic dimension of the matrix composition so as to retain the matrix composition inside the pouch before use and/or to retain a part of the matrix composition, such as an insoluble composition, inside the pouch during use.

In order to obtain a pouch having suitable opening dimensions in view of the matrix composition to be used, the material for the pouch may be selected accordingly, e.g. comprising e.g. wowen or non-wowen fabric.

In other words, according to the various embodiments, the pouch forms a membrane allowing passage of saliva and prevents or inhibits passage of said water-insoluble composition. The membrane of the pouch may be of any suitable material e.g. wowen or non-wowen fabric (e.g. cotton, fleece etc.), heat sealable non-wowen cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of cannabinoids from the pouch.

The powder is filled into pouches and is maintained in the pouch by a sealing. An ideal pouch is chemically and physically stable, it is pharmaceutically acceptable, it is insoluble in water, it is easy to fill with powder and seal, and it provides a semi-permeable membrane layer which prevent the powder from leaving the bag, but permit saliva and therein dissolved or sufficiently small suspended components from the powder in the pouch, such as cannabinoids, to pass through said pouch.

The pouch may be placed in the oral cavity by the user. Saliva then enters into the pouch, and the one or more cannabinoids and other components, which are soluble in saliva, start to dissolve and are transported with the saliva out of the pouch into the oral cavity, where the cannabinoid may be absorbed.

According to an embodiment of the invention, the matrix composition may further comprise one or more enhancers.

In an embodiment of the invention, said enhancers are selected from the group consisting of bile salts, cetomacrogols, chelating agents, citrates, cyclodextrins, detergents, enamine derivatives, fatty acids, labrasol, lecithins, phospholipids, syntetic and natural surfactants, nonionic surfactants, cell envelope disordering compounds, solvents, steroidal detergents, chelators, solubilization agents, charge modifying agents, pH control agents, degradative enzyme inhibitors, mucolytic or mucus clearing agents, membrane penetration-enhancing agents, modulatory agents of epithelial junction physiology, vasodilator agents, selective transport-enhancing agents, or any combination thereof. pH control agents include buffers.

In an embodiment of the invention, said enhancers are selected from the group consisting of cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids (C.sub.8-C.sub.18) ethoxylated Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phophatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil, Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, NOC5 [3-(2-hydroxy-1-(methyl-ethyl)-2-nitrosohydrazino)-1-propanamine], NOC12 [iV-ethyl-2-(1-ethyl-hydroxy-2-nitrosohydrazino)-ethanamine, SNAP [S-nitroso-N-acetyl-DL-penicilamine, NORI, NOR4, deacylmethyl sulfoxide, azone, salicylamide, glyceryl-1,3-diacetoacetate, 1,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropylβ-cyclodetran, Sulfobutylether-β-cyclodextran, Methylβ-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl)hexanolamine, Propylene glycol, Tetradecylmaltoside (TDM), Sucrose dedecanoate.

According to an embodiment of the invention, the enhancer comprises one or more pH control agent, such as a buffering agent.

In an embodiment of the invention, said pH control agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to an embodiment of the invention, the water-insoluble composition comprises cellulose, e.g. as a carrier.

In an embodiment of the invention the cellulose is or comprises microcrystalline cellulose.

One advantage of the above embodiment may be that microcrystalline cellulose may absorb a relatively high amount of cannabinoid, while also allowing for the one or more cannabinoids to be effectively released from the pouch during use.

The cellulose may be synthetic or semisynthetic celluloses, or it may be derived from natural celluloses. It is normally crystalline such as microcrystalline. Certain specific embodiments may also utilize other forms of carriers, in addition to or including mcc, such as but not limited to fibrous material or carbohydrates including cellulose (including hemicellulose, celluloses with different crystallinities and structures (e.g. varying structures including solid fibers, and addition or including fibers or the like in various structures such as web-like structures and/or other structures), including naturally occurring celluloses including *Cladophora* sp. Algae cellulose or the like), dextran, agarose, agar, pectin, alginate, xanthan, chitosan, starch (including potato starch, shoti starch) etc. or mixtures thereof.

The microcrystalline cellulose may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

In an embodiment of the invention said cellulose is provided in the form of particles having an average particle size between 1 and 1000 micrometers, such as between 10 and 250 micrometers, such as between 15 and 200 micrometers, such as between 20 and 150 micrometers, such as between 50 and 100 micrometers, such as about 75 micrometers.

In an embodiment of the invention said cellulose has a specific surface area of between 0.65 and 1.5 $m^2/g$, such as between 0.75 and 1.25 $m^2/g$, such as between 0.85 and 1.15 $m^2/g$, such as between 0.9 and 1.1 $m^2/g$, such as about 0.95 $m^2/g$, about 1.00 $m^2/g$, or such as about 1.05 $m^2/g$.

In an embodiment of the invention said cellulose has a bulk density between 0.1 and 1.0 grams per cubic centimeter ($g/cm^3$), such as between 0.25 and 0.5 grams per cubic centimeter, such as between 0.26 and 0.31 grams per cubic centimeter, or such as between 0.28 and 0.33 grams per cubic centimeter.

In the context of the above embodiment it should preferably be understood that the bulk density of the cellulose is understood as the bulk density at about 25 degrees Celsius.

In an embodiment of the invention said cellulose has a porosity characterized by an average specific pore volume between 0.003 $cm^3/g$ and 0.60 $cm^3/g$, such as between 0.01 and 0.3 $cm^3/g$.

In an embodiment of the invention said cellulose has a moisture content of less than about 5% by weight, such as between 2 and 5% by weight, such as between 3 and 5% by weight, such as about 4% by weight.

Various types of usable cellulose includes microcrystalline cellulose (MCC); carboxymethylcellulose (CMC), such as sodium carboxymethylcellulose; hydroxypropyl methylcellulose (HPMC), methylcellulose; ethylcellulose (EC); methylethylcellulose (MEC); hydroxyethyl cellulose (HEC); hydroxyethyl methylcellulose (NEMC); and any combination thereof.

In an embodiment of the invention said cellulose has an average fiber size of less than 200 micrometers, such as between 75 and 125 micrometers, or such as below 75 micrometers.

In an embodiment of the invention the cellulose comprises pores, the pores having an average pore size of between about 3 nanometers and about 300 nanometers, such as between 10 nanometers and 200 nanometers, such as between 20 nanometers and 100 nanometers.

In an embodiment of the invention said cellulose is derived from natural sources, such as wood pulp.

Other examples of natural sources of cellulose include sugar beet fiber, cotton fiber, bran fiber, citrus pulp fiber, grass fiber, willow fiber, poplar fiber, bamboo fiber, and combinations thereof, or combinations thereof with wood pulp.

In some embodiments, the cellulose can be chemically treated, e.g. by means of CMC, MPMC, HPC, MCC, and/or other methods.

Alternatively, the cellulose may be semi-synthetic or synthetic cellulose.

According to an embodiment of the invention the water-insoluble composition comprises an ion-exchange resin, such as a basic ion-exchange resin, e.g. a strongly basic ion-exchange resin.

The ion-exchange resin, such as the basic ion-exchange resin, of the water-insoluble composition may be part of the carrier when the matrix composition comprises a carrier.

The one or more cannabinoids may, especially when using a basic ion-exchange resin, be selected from the cannabinoids having at least one phenolic moiety. By using cannabinoid(s) having at least one phenolic moiety, the basic group of the basic ion exchange resin has one or more groups on the cannabinoid(s) to bind with. The cannabinoid(s) may in some embodiment optionally comprise one or more carboxylic groups, thus adding to the potential binding sites for the basic ion exchange resin.

In an embodiment of the invention the ion exchange resin(s) acts as a stabilization agent.

One very important advantage of the above embodiment may be that the amount of cannabinoid(s) available for body uptake is advantageously preserved due to the stabilization of the cannabinoid(s).

In an advantageous embodiment of the invention the basic ion exchange resin comprises strongly basic ion exchange resin.

One advantage of the above embodiment may be that a relatively effective stabilization of the cannabinoid(s) may be achieved, while synchronized release of the cannabinoid(s) from the complex, i.e. synchronized with the intended time of delivery to the body may be achieved, e.g. in one embodiment by adding an acid to the pouch.

In an advantageous embodiment of the invention the basic ion exchange resin is strongly basic ion exchange resin.

One advantage of the above embodiment may be that a relatively effective stabilization of the cannabinoid(s) may be achieved, while synchronized release of the cannabinoid(s) from the complex, i.e. synchronized with the intended time of delivery to the body may be achieved, e.g. in one embodiment by adding an acid to the pouch.

In an advantageous embodiment of the invention the basic ion exchange resin comprises weakly basic ion exchange resin.

One advantage of the above embodiment may be that a relatively effective release of the cannabinoid(s) from the complex may be obtained, in some embodiments without using any agents, such as acids, for facilitating release of the cannabinoid(s) from the complex.

In an advantageous embodiment of the invention said basic ion exchange resin is a strongly basic ion exchange resin comprising one or more quaternary amino groups.

Examples of strongly basic ion exchange resins include for example commercially available products, such as Ambersep® 900, Cholestyramine, and Duolite AP143.

In an advantageous embodiment of the invention the basic ion exchange resin are selected from the group consisting of Ambersep 900, Cholestyramine, Duolite AP143, Amberlite CG-400, Amberlite IRA-400, Amberlite IRA-401, Amberlite IRA-410, Amberlite IRA-900, and Amberlite IRA-904.

In an advantageous embodiment of the invention the basic ion exchange resin comprises cross-linked polystyrene.

In an advantageous embodiment of the invention the basic ion exchange resin comprises cross-linked polystyrene, wherein the cross-linking agent comprises or is divinylbenzene.

In an advantageous embodiment of the invention the basic ion exchange resin comprises a styrene-divinylbenzene copolymer.

According to an embodiment of the invention, the basic ion exchange resin is a styrene-divinylbenzene copolymer functionalized by basic groups, such as amine groups. If a strongly basic ion exchange resin is desirable, strongly basic functional groups, such as quaternary amines, are used; whereas if a weakly basic ion exchange resin is desirable, weakly basic functional groups, such a primary, secondary, or tertiary amine groups, are used.

In an advantageous embodiment of the invention the basic ion exchange resin has a counter ion selected from the group consisting of hydroxide, chloride, and bromide, before reaction with the one or more cannabinoids.

According to various embodiments of the invention, sugar alcohols may be included in the pouch as a matrix composition or part thereof as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch comprises bulk sweeteners including sugar and/or sugarless components.

In an embodiment of the invention, the pouch comprises bulk sweetener in the amount of 5 to about 95% by weight of the pouch, more typically constitute 20 to about 80% by weight of the pouch, and more commonly, 30 to 60% by weight of the pouch. Bulk sweeteners may function both as a sweetener and also as a humectant.

The sweeteners may often support the flavor profile of the pouch.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In an embodiment of the invention the pouch comprises flavor. Flavor may typically be present in amounts between 0.01 and 10% by weight of the total composition of the pouch, such as between 0.01 and 5% by weight of the total composition.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In various embodiments of the invention, the matrix composition comprises a release controlling composition for controlling the release of the matrix composition and/or parts thereof, especially the one or more cannabinoids.

The release controlling composition may, according to various embodiments, be selected group consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil and mixtures thereof. Particularly, metallic stearates, such as magnesium stearate may be advantageous.

According to an embodiment of the invention said modified calcium carbonate is made according to US patent application US 2012/0039981 A1, hereby incorporated by reference, particularly as in the examples therein.

The release controlling composition may be added to the matrix composition in various ways.

For example, the release controlling composition may be added by full powder mixture during the last few minutes of the final mixing.

Alternatively, the release controlling composition may be added after the granulation steps on a granulation premix.

Still further, the release controlling composition may be added only as a fraction of the matrix composition so two different release profiles of cannabinoids are achieved. Even further two or more fractions of the matrix composition may comprise different amounts of the release controlling composition, if any, thereby providing a more complex and tailored release profile of cannabinoids.

The release controlling composition, such as magnesium stearate, may have a sealing effect and can be used to control the release of the one or more cannabinoids and the solubility of the matrix composition.

According to an embodiment of the invention, the pouch comprises polyvinylpyrrolidone (PVP).

One advantage of the above embodiment may be that a more uniform composition may be obtained.

EXAMPLES

The following examples are illustrative of the present invention and should not be considered as limiting the scope of the invention.

Examples 1-3 illustrate various raw materials and methods for preparing intermediate ingredients.

Examples 4-8 discloses a number of different pouches and their respective compositions.

Example 1

Preparation of Cannabinoid Powder Composition

Cannabinoids come in different grades and form from pasta, oil and crystals and in different concentrations. Depending on the form of cannabinoids the manufacturing steps will vary.

As illustrated in the following examples, cannabinoids can be added as powder or sorbed, mixed or granulated on different carriers as microcrystalline cellulose (MCC) or sugar alcohols etc.

Example 2

Preparation of Pouches Designed for Administration of Cannabinoids

The material of the pouches is heat sealable non-wowen cellulose.

The powder is filled into pouches and is maintained in the pouch by a sealing.

Example 3

Preparation of Pouches with Water-Insoluble Composition

Cannabinoids used in example 3 are obtained in accordance with example 1. The pouches described in example 2 are used.

Herein, target fill weight 400 mg powder per pouch. Alternatively, target fill weights of e.g. 250 mg or 800 mg could be used.

Example 3.1

The cannabinoids are dissolved in ethanol with a weight ratio of about 1:1 to form a homogeneous granulation solution. The granulation solution is slowly added to the microcrystalline cellulose under stirring (Kitchenaid mixer operated at about 30 RPM in about 30 minutes). The resulting granulate is sieved and placed on a tray. The resulting powder is dried at ambient temperature overnight and is thereafter sieved.

A fine-grained powder of cannabinoids-microcrystalline cellulose carrier complex was obtained.

The obtained cannabinoids-microcrystalline cellulose carrier complex is mixed with the remaining ingredients to obtain a final powder composition.

The final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. MCC and/or sugar alcohols, these further humectants are added in the same manner as magnesium stearate.

Example 3.2

The cannabinoids are dissolved in ethanol with a weight ratio of about 1:1 and the Kollidon 25 (polyvinylpyrrolidone) is added together with the liquid flavor to form a homogeneous granulation solution.

The following solid components are mixed and sieved to form a powder mixture: mannitol, MCC, high intensive sweetener and flavors.

The granulation solution is slowly added to the powder mixture under stirring (Kitchenaid mixer operated at about 30 RPM in about 30 minutes). The resulting granulate is sieved and placed on a tray. The resulting powder is dried at ambient temperature overnight and is thereafter sieved to obtain a final powder composition.

The final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. MCC and/or sugar alcohols, these further humectants are added in the same manner as magnesium stearate.

Example 3.3

The ion exchange resin complex is made by dissolving the cannabinoids (882 g CBD) in 88 L ethanol to form a homogeneous solution. NaOH can be added to make the binding of the cannabinoid(s) and the ion-exchange resin better.

5 kg of ion exchange resin (Ambersep 900 on OH-form) is added. When all the CBD solution has been bound by the ion exchange resin the pressure is reduced and the obtained mixture is concentrated in vacuo at elevated temperature affording the desired complex as a powder.

The obtained powder is mixed with the remaining ingredients to obtain a final powder composition. An acid like citric acid can be added to increase the release of the cannabinoid(s) from the resin during usage.

The final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Glycerin may also be added, for example in amounts giving a ratio of glycerin to ion exchange resin of about 1 to 3.4.

Example 3.4

A powder composition obtained the same way as the final powder competition in example 3.3. Thereafter, polyvinylpyrrolidone (Kollidon 25) is added to form a granulation solution. The resulting granulate is sieved and placed on a tray. The resulting powder is dried at ambient temperature overnight and is thereafter sieved to obtain a final powder composition.

The final powder composition manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 4

Preparation of Pouches with Water-Insoluble Composition

TABLE 1

| | Pouch no. | | | | | | |
| --- | --- | --- | --- | --- | --- | --- | --- |
| | 101 | 102 | 103 | 104 | 105 | 106 | 107 |
| | Method cf. example | | | | | | |
| | 3.1 | 3.1 | 3.2 | 3.3 | 3.3 | 3.4 | 3.4** |
| Raw material | Content in weight percent | | | | | | |
| CBD extract | 5.00* | 5.00* | 5.00* | 5.00* | 5.00* | 5.00* | 5.00* |
| NaOH | — | — | — | — | — | — | 0.60 |
| Citric acid | — | — | — | — | — | — | 0.70 |
| Mannitol | 43.45 | 73.45 | 65.45 | 43.45 | 73.45 | 65.45 | 64.15 |
| MCC | 50.00 | 20.00 | 20.00 | — | — | — | — |
| Ion exchange resin | — | — | — | 50.00 | 20.00 | 20.00 | 20.00 |
| Flavor | 1.50 | 1.50 | 1.50 | 1.50 | 1.50 | 1.50 | 1.50 |
| HIS | 0.05 | 0.05 | 0.05 | 0.05 | 0.05 | 0.05 | 0.05 |
| PVP | — | — | 8.00 | — | — | 8.00 | 8.00 |
| Total | 100 | 100 | 100 | 100 | 100 | 100 | 100 |

Cannabinoid pouch; CBD used is a 50% extract.

*5% CBD corresponds to 10 mg CBD/pouch.

Pouches contain 400 mg per piece.

MCC is microcrystalline cellulose.

Ion exchange resin is an Ambersep 900 on OH-form.

HIS = High intense sweetener may for example be sucralose.

Flavor may for example be pepper mint flavor.

PVP = polyvinylpyrrolidone, Kollidon 25.

As shown in table 1, different water-insoluble compositions may be used, including MCC and ion-exchange resin, and in different amounts. Possible inclusion of PVP is also shown, as well as inclusion of base (here NaOH) and acid (here citric acid) when using ion exchange resin.

Example 5

Preparation of Pouched with Magnesium Stearate

TABLE 2

| | Pouch no. | | |
|---|---|---|---|
| | 108 | 109 | 110 |
| | Method cf. example | | |
| | 3.1 | 3.3 | 3.4 |
| Raw material | Content in weight percent | | |
| CBD extract | 5.00* | 5.00* | 5.00* |
| Mannitol | 63.45 | 63.45 | 55.45 |
| MCC | 20.00 | — | — |
| Ion exchange resin | — | 20.00 | 20.00 |
| Flavor | 1.50 | 1.50 | 1.50 |
| HIS | 0.05 | 0.05 | 0.05 |
| PVP | — | — | 8.00 |
| MgSt | 10.00 | 10.00 | 10.00 |
| Total | 100 | 100 | 100 |

Cannabinoid pouch; CBD used is a 50% extract.
*5% CBD corresponds to 10 mg CBD/pouch.
Pouches contain 400 mg per piece.
MCC is microcrystalline cellulose.
Ion exchange resin is an Ambersep 900 on OH-form.
HIS = High intense sweetener may for example be sucralose.
Flavor may for example be pepper mint flavor.
PVP = polyvinylpyrrolidone, Kollidon 25.
MgSt is magnesium stearate and is added as a release controlling composition.

As shown in table 2, magnesium stearate (MgSt) can be included in the pouch in combination with both MCC and ion exchange resin. Magnesium stearate has a sealing effect and can be used to control the release of CBD and the solubility of the matrix composition. PVP may also be included.

Example 6

Preparation of Pouched with Different Cannabinoids and Different Purifications

TABLE 3

| | Pouch no. | | | | |
|---|---|---|---|---|---|
| | 111 | 112 | 113 | 114 | 115 |
| | Method cf. example | | | | |
| | 3.1 | 3.1 | 3.1 | 3.1 | 3.1 |
| Raw material | Content in weight percent | | | | |
| CBD pure (99.5%) | 2.51 | — | — | — | 2.51 |
| CDB extract (50%) | — | 5.00 | — | — | — |
| CDB extract (10%) | — | — | 25.00 | — | — |
| THC pure (99.5%) | — | — | — | 2.51 | 2.51 |
| Mannitol | 75.94 | 73.45 | 53.45 | 75.94 | 68.43 |
| MCC | 20.00 | 20.00 | 20.00 | 20.00 | 20.00 |
| Flavor | 1.50 | 1.50 | 1.50 | 1.50 | 1.50 |

TABLE 3-continued

| | Pouch no. | | | | |
|---|---|---|---|---|---|
| | 111 | 112 | 113 | 114 | 115 |
| | Method cf. example | | | | |
| | 3.1 | 3.1 | 3.1 | 3.1 | 3.1 |
| Raw material | Content in weight percent | | | | |
| HIS | 0.05 | 0.05 | 0.05 | 0.05 | 0.05 |
| MgSt | — | — | — | — | 5 |
| Total | 100 | 100 | 100 | 100 | 100 |

Cannabinoid pouch; CBD used corresponds to 10 mg CBD/pouch.
THC used corresponds to 10 mg THC/pouch.
Pouches contain 400 mg per piece.
MCC is microcrystalline cellulose.
HIS = High intense sweetener may for example be sucralose.
Flavor may for example be pepper mint flavor.
MgSt is magnesium stearate and is added as a releasing agent.

As shown in table 3, different cannabinoids, CBD and THC, may be used. Also, different concentrations of the cannabinoids may be used, here illustrated as 10% extract, 50% extract, or 99.5% pure cannabinoids. Finally, different cannabinoids may be combined, here shown by a combination of CBD and THC.

Example 7

Preparation of Pouches with Different Concentrations of Cannabinoids When Using Pure CBD (99.5%)

TABLE 4

| | Pouch no. | | | | |
|---|---|---|---|---|---|
| | 116 | 117 | 118 | 119 | 120 |
| | Method cf. example | | | | |
| | 3.2 | 3.2 | 3.2 | 3.2 | 3.2 |
| | Amount of cannabinoids | | | | |
| | 5 mg | 10 mg | 20 mg | 50 mg | 100 mg |
| Raw material | Content in weight percent | | | | |
| CDB | 1.26 | 2.51 | 5.03 | 12.56 | 25.13 |
| Isomalt | 64.19 | 62.94 | 60.42 | 42.89 | 30.32 |
| MCC | 20.00 | 20.00 | 20.00 | 30.00 | 30.00 |
| Flavor | 1.50 | 1.50 | 1.50 | 1.50 | 1.50 |
| HIS | 0.05 | 0.05 | 0.05 | 0.05 | 0.05 |
| PVP | 8.00 | 8.00 | 8.00 | 8.00 | 8.00 |
| MgSt | 5.00 | 5.00 | 5.00 | 5.00 | 5.00 |
| Total | 100 | 100 | 100 | 100 | 100 |

Cannabinoid pouch; CBD is used in different dosage from 5-100 mg CBD/pouch - CBD extract of 99.5% has been used.
Pouches contain 400 mg per piece.
MCC is microcrystalline cellulose.
HIS = High intense sweetener may for example be sucralose.
Flavor may for example be pepper mint flavor.
MgSt is magnesium stearate and is added as a releasing agent.
PVP = polyvinylpyrrolidone, Kollidon 25.
CBD could be replaced with THC or be in combination with THC.

When using CBD (50% pure):

TABLE 5

| Raw material | Pouch no. | | | | |
|---|---|---|---|---|---|
| | 121 | 122 | 123 | 124 | 125 |
| | Method cf. example | | | | |
| | 3.2 | 3.2 | 3.2 | 3.2 | 3.2 |
| | Amount of cannabinoids | | | | |
| | 5 mg | 10 mg | 20 mg | 50 mg | 100 mg |
| | Content in weight percent | | | | |
| CDB | 2.50 | 5.00 | 10.00 | 25.00 | 50.00 |
| Isomalt | 62.95 | 60.45 | 55.45 | 30.45 | 5.45 |
| MCC | 20.00 | 20.00 | 20.00 | 30.00 | 30.00 |
| Flavor | 1.50 | 1.50 | 1.50 | 1.50 | 1.50 |
| HIS | 0.05 | 0.05 | 0.05 | 0.05 | 0.05 |
| PVP | 8.00 | 8.00 | 8.00 | 8.00 | 8.00 |
| MgSt | 5.00 | 5.00 | 5.00 | 5.00 | 5.00 |
| Total | 100 | 100 | 100 | 100 | 100 |

Cannabinoid pouch; CBD is used in different dosage from 5-100 mg CBD/pouch - CBD extract of 50% has been used.
Pouches contain 400 mg per piece.
MCC is microcrystalline cellulose.
HIS = High intense sweetener may for example be sucralose.
Flavor may for example be pepper mint flavor.
MgSt is magnesium stearate and is added as a releasing agent.
PVP = polyvinylpyrrolidone, Kollidon 25.
CBD could be replaced with THC or be in combination with THC.

As shown in tables 4-5, different total amounts of cannabinoids (here CBD) may be used in the pouch, regardless of using relatively pure cannabinoids or if using an extract comprising other components.

Example 8

Preparation of Pouches with Different Humectants

TABLE 6

| Raw material | Pouch no. | | | |
|---|---|---|---|---|
| | 126 | 127 | 128 | 129 |
| | Method cf. example | | | |
| | 3.1 | 3.1 | 3.1 | 3.1 |
| | Content in weight percent | | | |
| CBD extract | 5.00* | 5.00* | 5.00* | 5.00* |
| Isomalt | 73.45 | 71.45 | 71.45 | 71.45 |
| MCC | 20.0 | 20.0 | 20.0 | 20.0 |
| Flavor | 1.50 | 1.50 | 1.50 | 1.50 |
| HIS | 0.05 | 0.05 | 0.05 | 0.05 |
| Glycerol | — | 2.00 | — | — |
| Sodium alginate | — | — | 2.00 | — |
| Pectin | — | — | — | 2.00 |
| Total | 100 | 100 | 100 | 100 |

Cannabinoid pouch; CBD used is a 50% extract.
*5% CBD corresponds to 10 mg CBD/pouch.
Pouches contain 400 mg per piece.
MCC is microcrystalline cellulose.
HIS = High intense sweetener may for example be sucralose.
Flavor may for example be pepper mint flavor.
Glycerol, sodium alginate and pectin are action as moistening or lubricant agent.

As shown in table 6, different further humectants may be added. Humectants attract the saliva from the mouth and make sure that water is available in the pouch. Increased water increase the release.

Example 9

Evaluation

The pouches produced were evaluated and found highly suitable as delivery vehicles for cannabinoids.

What is claimed is:

1. A pouch designed for administration of an active ingredient in the oral cavity, the pouch comprising a powder composition comprising:
   an amount of one or more cannabinoids; and
   a water-insoluble composition comprising cellulose in the form of particles in an amount of 30 to 80% by weight of the powder composition,
   wherein the powder composition further comprises a water-soluble composition comprising one or more sugar alcohols, and wherein the pouch comprises a water-permeable membrane, wherein said cellulose is selected from the group consisting of microcrystalline cellulose (MCC), carboxymethylcellulose (CMC), sodium carboxymethylcellulose, hydroxypropyl methylcellulose (HPMC), methylcellulose, ethylcellulose (EC), methylethylcellulose (MEC), hydroxyethyl cellulose (HEC), hydroxyethyl methylcellulose (HEMC), and combinations thereof.

2. The pouch according to claim 1, wherein the powder composition comprises said water-insoluble composition in an amount of between 30 and 60 percent by weight of said powder composition.

3. The pouch according to claim 1, wherein said cellulose is synthetic or semisynthetic cellulose.

4. The pouch according to claim 1, wherein said cellulose is derived from natural cellulose.

5. The pouch according to claim 1, wherein said cellulose includes naturally occurring celluloses.

6. The pouch according to claim 1, wherein said cellulose has a bulk density between 0.1 and 1.0 grams per cubic centimeter ($g/cm^3$).

7. The pouch according to claim 1, wherein the powder composition comprises a release controlling composition in an amount of between 1 and 20 percent by weight of said powder composition.

8. The pouch according to claim 1, wherein the one or more cannabinoids is physically or chemically bound to at least a part of the powder composition acting as a carrier.

9. The pouch according to claim 1, wherein the one or more cannabinoids comprises cannabidiol.

10. The pouch according to claim 1, wherein the one or more cannabinoids comprises tetrahydrocannabinol.

11. The pouch according to claim 1, wherein the pouch further comprises a humectant.

12. The pouch according to claim 1, wherein the pouch further comprises a humectant selected from the group consisting of xanthan gum, pectin, alginate, and combinations thereof.

13. A pouch designed for administration of an active ingredient in the oral cavity, the pouch containing a matrix composition comprising:
   a powder composition comprising
      an amount of one or more cannabinoids;
      a water-soluble composition comprising one or more sugar alcohols; and
      a water-insoluble composition comprising cellulose in the form of particles having an average particle size between 1 and 1200 micrometers,
   wherein the pouch comprises a water-permeable membrane, wherein said cellulose is selected from the group consisting of microcrystalline cellulose (MCC), carboxymethylcellulose (CMC), sodium carboxymethylcellulose, hydroxypropyl methylcellulose (HPMC), methylcellulose, ethylcellulose (EC), methylethylcellulose (MEC), hydroxyethyl cellulose (HEC), hydroxyethyl methylcellulose (HEMC), and combinations thereof.

14. A pouch designed for administration of an active ingredient in the oral cavity, the pouch containing a powdered matrix composition comprising:
   an amount of one or more cannabinoids;
   a water-soluble composition comprising one or more sugar alcohols; and
   a water-insoluble composition comprising cellulose having a specific surface area of between 0.65 and 1.5 $m^2/g$,
   wherein the one or more cannabinoids is physically or chemically bound to at least a part of the powdered matrix composition acting as a carrier, wherein the pouch comprises a water-permeable membrane, and wherein said cellulose is selected from the group consisting of microcrystalline cellulose (MCC), carboxymethylcellulose (CMC), sodium carboxymethylcellulose, hydroxypropyl methylcellulose (HPMC), methylcellulose, ethylcellulose (EC), methylethylcellulose (MEC), hydroxyethyl cellulose (HEC), hydroxyethyl methylcellulose (HEMC), and combinations thereof.

15. The pouch according to claim 13, wherein the water-permeable membrane is a woven fabric.

16. The pouch according to claim 13, wherein the water-permeable membrane is a non-woven fabric.

17. The pouch according to claim 13, wherein the matrix composition comprises said one or more cannabinoids in an amount of 0.25 to 500 milligrams.

18. The pouch according to claim 14, wherein the one or more cannabinoids is physically or chemically bound to at least a part of the matrix composition acting as a carrier.

19. The pouch according to claim 14, wherein the matrix composition comprises said water-insoluble composition in an amount of between 1 and 80 percent by weight of said matrix composition.

* * * * *